US010912536B2

(12) United States Patent
Lalena

(10) Patent No.: US 10,912,536 B2
(45) Date of Patent: Feb. 9, 2021

(54) ULTRASOUND SYSTEM AND METHOD

(71) Applicant: CARESTREAM HEALTH, INC., Rochester, NY (US)

(72) Inventor: Michael C. Lalena, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 454 days.

(21) Appl. No.: 15/681,887

(22) Filed: Aug. 21, 2017

(65) Prior Publication Data

US 2018/0055479 A1 Mar. 1, 2018

Related U.S. Application Data

(60) Provisional application No. 62/378,279, filed on Aug. 23, 2016.

(51) Int. Cl.
*A61B 8/00* (2006.01)
*A61B 8/14* (2006.01)
(Continued)

(52) U.S. Cl.
CPC .............. *A61B 8/14* (2013.01); *A61B 8/085* (2013.01); *A61B 8/0825* (2013.01); *A61B 8/4209* (2013.01); *A61B 8/4461* (2013.01); *A61B 8/463* (2013.01); *A61B 8/54* (2013.01); *G01S 7/52098* (2013.01); *G06T 7/20* (2013.01); *A61B 8/4405* (2013.01); *A61B 8/4444* (2013.01); *A61B 8/4455* (2013.01); *A61B 8/4466* (2013.01); *A61B 8/4477* (2013.01); *A61B 8/4483* (2013.01); *A61B 8/4494* (2013.01); *A61B 8/467* (2013.01); *A61B 8/481* (2013.01); *A61B 8/5246* (2013.01); *A61B 8/5276* (2013.01);
(Continued)

(58) Field of Classification Search
CPC ....... A61B 6/032; A61B 6/469; A61B 8/4483; A61B 8/4444; A61B 8/4455; A61B 8/4461; A61B 8/4466; A61B 8/4494; A61B 8/4477; G06K 9/20; G06K 2209/05
See application file for complete search history.

(56) References Cited

U.S. PATENT DOCUMENTS 5,370,120 A 12/1994 Oppelt et al.
6,705,995 B1 3/2004 Poland et al.
(Continued)

FOREIGN PATENT DOCUMENTS

CN 102930170 2/2013
WO 2006/111874 10/2006
(Continued)

OTHER PUBLICATIONS

Thomas L. Szabo et al., "Ultrasound Transducer Selection in Clinical Imaging Practice," 2013, J. Ultrasound Med, 32, pp. 573-582.

*Primary Examiner* — Elmer M Chao

(57) ABSTRACT

A method for ultrasound imaging detects a region of interest from ultrasound signals of a first imaging mode received along sensing elements of a transducer probe. The sensed data is analyzed and the system responds to the region of interest detection by switching to a secondary imaging mode with the transducer probe at the same position. The transducer probe indexes to a next scan position and sensing and analysis are repeated at each of a number of indexed scan positions.

16 Claims, 11 Drawing Sheets

(51) Int. Cl.
  *G06T 7/20* (2017.01)
  *A61B 8/08* (2006.01)
  *G01S 7/52* (2006.01)
  *G01S 15/89* (2006.01)

(52) U.S. Cl.
  CPC . *G01S 15/8979* (2013.01); *G06T 2207/10132* (2013.01); *G06T 2207/20104* (2013.01)

(56) References Cited

U.S. PATENT DOCUMENTS

| | | | |
|---|---|---|---|
| 7,534,211 B2 | 5/2009 | Hwang et al. | |
| 8,285,357 B2 | 10/2012 | Gardner et al. | |
| 8,496,586 B2 | 7/2013 | Zhang et al. | |
| 9,180,898 B2 | 11/2015 | Ninomiya et al. | |
| 9,597,041 B2 | 3/2017 | Claus et al. | |
| 2005/0113689 A1 | 5/2005 | Gritzky | |
| 2005/0197572 A1* | 9/2005 | Williams | A61B 8/06 600/437 |
| 2005/0288587 A1* | 12/2005 | Roh | A61B 8/4461 600/445 |
| 2007/0078345 A1* | 4/2007 | Mo | A61B 8/12 600/459 |
| 2008/0161688 A1 | 7/2008 | Poland | |
| 2012/0095343 A1* | 4/2012 | Smith | G01S 15/8913 600/447 |
| 2013/0218012 A1* | 8/2013 | Specht | A61B 8/485 600/438 |
| 2014/0039317 A1 | 2/2014 | Sato | |
| 2015/0087979 A1* | 3/2015 | Zhang | A61B 8/4209 600/440 |
| 2016/0166238 A1 | 6/2016 | Oh et al. | |
| 2016/0310110 A1* | 10/2016 | Dodd | A61B 8/54 |
| 2016/0364527 A1 | 12/2016 | Reicher et al. | |

FOREIGN PATENT DOCUMENTS

| | | |
|---|---|---|
| WO | 2008/068710 | 6/2008 |
| WO | 2016/001865 | 1/2016 |

* cited by examiner

ULTRASOUND SYSTEM AND METHOD

CROSS REFERENCE TO RELATED APPLICATIONS

This application claims the benefit of U.S. Provisional application U.S. Ser. No. 62/378,279, provisionally filed on Aug. 23, 2016, entitled "ULTRASOUND SYSTEM AND METHOD", in the name of Michael C. Lalena, incorporated herein in its entirety.

TECHNICAL FIELD

The disclosure relates generally to the field of medical systems and methods and more particularly to a system and method for automated ultrasound scanning.

BACKGROUND

Ultrasound imaging systems/methods are known, such as those described, for example, in U.S. Pat. Nos. 6,705,995 (Poland), 5,370,120 (Oppelt), and 8,285,357 (Gardner), all of which are incorporated herein in their entirety. Various applications for diagnostic ultrasound systems are given, for example, in the article entitled "Ultrasound Transducer Selection In Clinical Imaging Practice", by Szabo and Lewin, *Journal of Ultrasound Medicine,* 2013; 32:573-582, incorporated herein by reference in its entirety.

Ultrasound utilizes sound waves at frequencies higher than those perceptible to the human ear. Ultrasonic images known as sonograms are generated as a result of pulsed ultrasonic energy that has been directed into tissue using a probe. The probe obtains echoed sound energy from the internal tissue and provides signal content that represents the different sound reflectivity exhibited by different tissue types. This signal content is then used to form images that visualize features of the internal tissue. Medical ultrasound, also known as diagnostic sonography or ultrasonography, is used as a diagnostic imaging technique used to help visualize features and operation of tendons, muscles, joints, vessels and internal organs of a patient.

FIGS. 1A-1B and FIGS. 2-3 show exemplary portable ultrasound systems 10 that use a cart/base/support, cart 12, a display/monitor 14, one or more input interface devices 16 (such as keyboard or mouse), and a generator 18. The display/monitor 14 can also be a touchscreen to function as an input device. As illustrated, the ultrasound system 10 can be a mobile or portable system designed to be wheeled from one location to another. As FIG. 2 shows, the ultrasound system 10 has a central processing unit CPU 20 that provides control signals and processing capabilities. CPU 20 is in signal communication with display 14 and interface device 16, as well as with a storage device 22 and an optional printer 24. A transducer probe 26 provides the ultrasound acoustic signal and generates an electronic feedback signal indicative of tissue characteristics from the echoed sound.

FIG. 3 shows an example of an ultrasound system 10 in use with an image provided on display/monitor 14.

Recent advances in ultrasound technology now provide advanced features on some systems, including automated ways to acquire scan data for particular types of exams. Reducing and minimizing the amount of operator activity and decision-making may help to improve productivity and to provide images that more effectively show patient condition. To address this need, ultrasound equipment manufacturers have introduced automated scanners that can repeatedly scan over the same tissue, two or more times, employing different signal types or using different transducer settings, pressure, speed, movement directions, and other variable settings.

However, there are some types of ultrasound imaging for which automation can be particularly challenging. Examples include imaging of the breast, in which it can be useful to obtain information from specific areas using multiple types of ultrasound signals. With repeated scanning over the same area, it can be very difficult to register one scan to another and to correlate information obtained for the same underlying tissue under different conditions.

Thus, it can be appreciated that there would be value in ultrasound imaging solutions that help to automate information capture for selective tissue, particularly where it is helpful to acquire data from the same region of interest under different signal conditions.

SUMMARY

An object of the present disclosure is to address the need for improved automation of ultrasound apparatus.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According to one aspect of the disclosure, there is provided a method for ultrasound imaging comprising: a) detecting a region of interest from ultrasound signals, of a first imaging mode, that have been received along sensing elements of a transducer probe, with the transducer probe at a first position; b) analyzing the sensed data and responding to the region of interest detection by switching to a secondary imaging mode, with the transducer probe at the same first position; c) indexing the transducer probe to a next scan position; and d) repeating steps a) through c) at each of a plurality of next indexed scan positions.

According to an alternate aspect, the present disclosure provides a method for ultrasound imaging of the breast, comprising: a) detecting ultrasound signals along a line of transducer probe sensing elements using ultrasound detection in a first operating mode, wherein the transducer probe is hinged to conform to the breast contour; b) analyzing the sensed data to detect a region of interest within the breast along the line of the transducer probe; c) responding to region of interest detection by switching to an alternate, secondary imaging mode before indexing the transducer probe to a next position; d) indexing the transducer probe to the next scan position following imaging in the secondary mode, wherein indexing is in a direction orthogonal to the line of the transducer probe sensing elements; and e) repeating steps a) through d) at each of a plurality of indexed scan positions.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE EMBODIMENTS

Figure 1B:
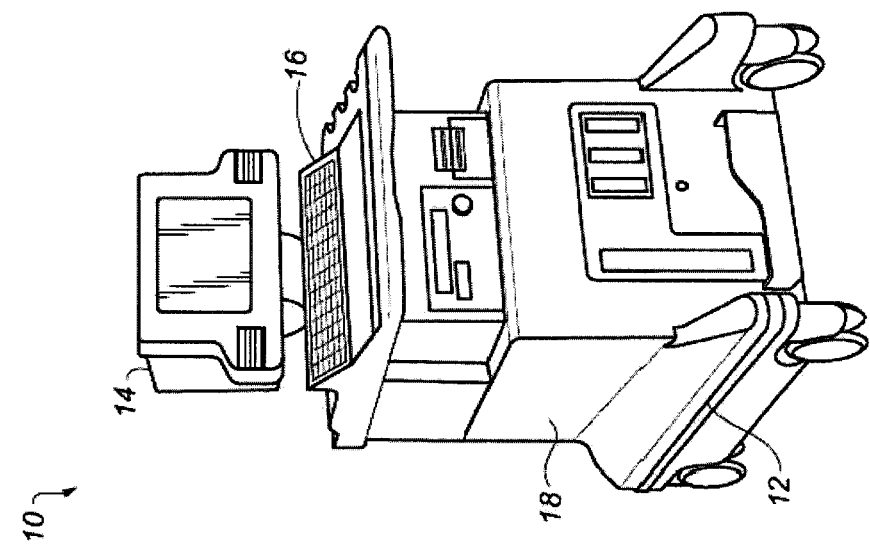
FIGS. 1A and 1B show exemplary ultrasound systems.

The following is a detailed description of the preferred embodiments, reference being made to the drawings in which the same reference numerals identify the same elements of structure in each of the several figures.

Different types of images, with different appearance, can be formed using sonographic apparatus. The familiar monochrome B-mode image displays the acoustic impedance of a two-dimensional cross-section of tissue. Other types of image can use color or other types of highlighting to display specialized information such as blood flow, motion of tissue over time, the location of blood, the presence of specific molecules, tissue stiffness, or the anatomy of a three-dimensional region.

Accordingly, the ultrasound systems of FIGS. 1A-3 are typically configured to be switchable for operation within at least two different ultrasound modes. As such, the system provides command entry or mechanical means to switch between at least two different ultrasound modes during an exam. Such multi-mode configurations, along with techniques for switching between modes, are known to those skilled in ultrasound technology.

Figure 1A:
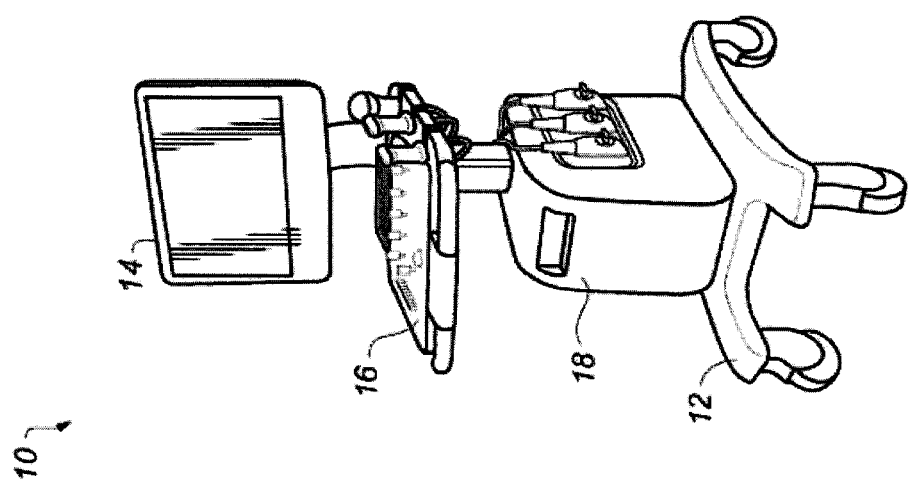
Figure 2:
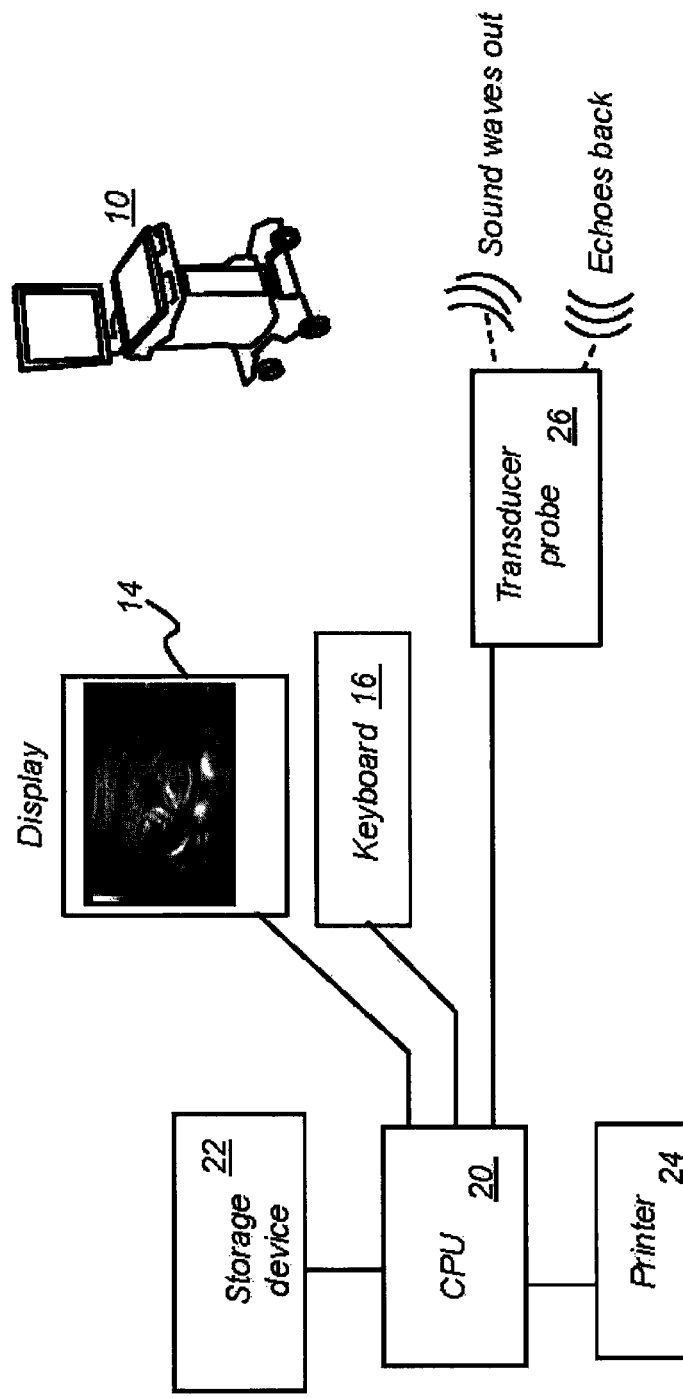
FIG. 2 shows a schematic of an exemplary ultrasound system.
Figure 3:
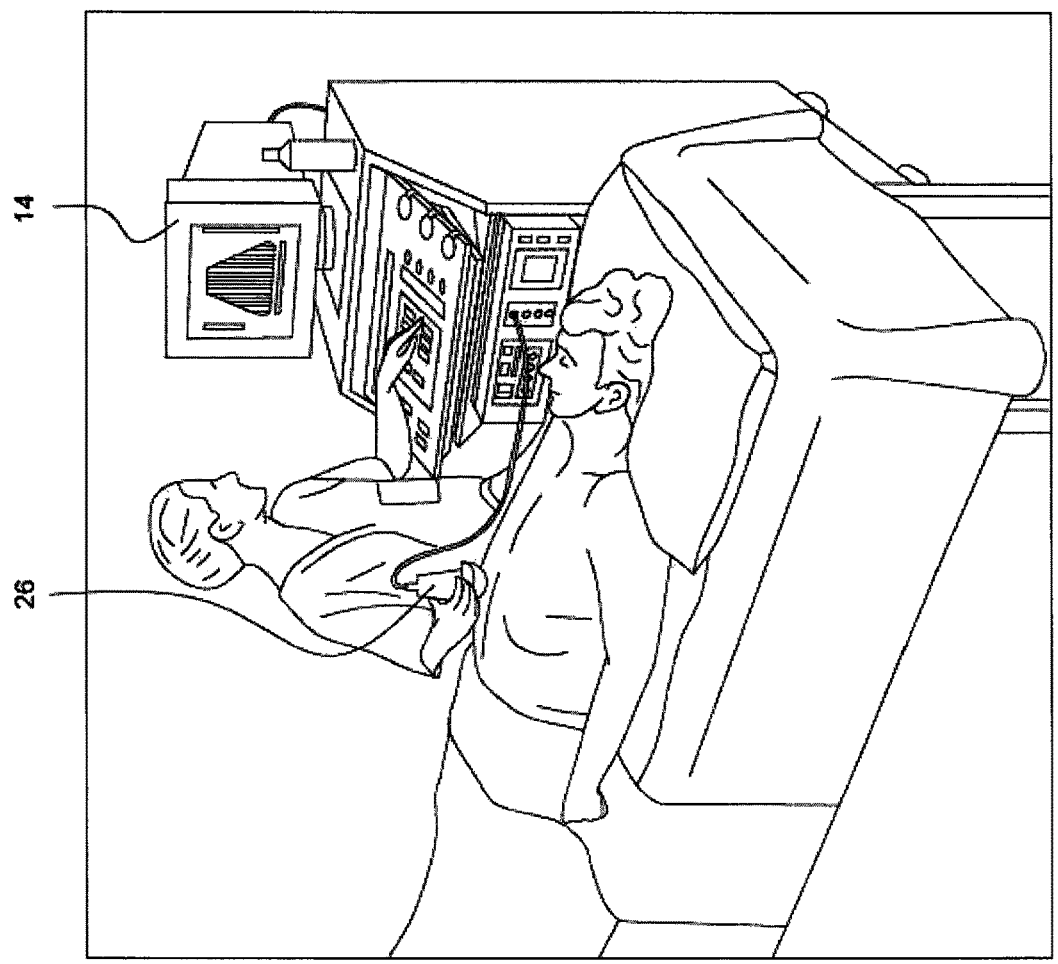
FIG. 3 illustrates a sonographer using an exemplary ultrasound system.

The ultrasound system 10, shown by way of example in FIGS. 1A and 1B, can include an image processing system, user interface device 16 and display monitor 14. The image processing system includes a memory and a processor. Additional, different or fewer components may be provided in the system or image processing system. In one embodiment, the system is a medical diagnostic ultrasound imaging system. The memory is a RAM, ROM, hard drive, removable media, compact disc, DVD, floppy disc, tape, cache memory, buffer, capacitor, combinations thereof or any other now known or later developed analog or digital device for storing information. The memory is operable to store data identifying a selected point for identifying a region of interest. The memory is operable to store data identifying one or a plurality of region of interest.

Information from the user interface indicating a position on an image on the display is used to determine a spatial relationship of a user selected point to a scanned region or image position. The selected point is an individual or single point in one embodiment that may be a point selected within a line, area or volume. Additional or different information may be also stored within the memory. The processor is general processor, application specific integrated circuit, digital signal processor, controller, field programmable gate array, digital device, analog device, transistors, combinations thereof or other now known or later developed devices for receiving analog or digital data and outputting altered or calculated data. The user input is a track ball, mouse, joy stick, touch pad, buttons, slider, knobs, position sensor, combinations thereof or other now known or later developed input devices. The user input is operable to receive a selected point from a user. For example, the user positions a cursor on an image displayed on the display. The user then selects a position of the cursor as indicating a point for a region of interest. The display can be a CRT, LCD, plasma screen, projector, combinations thereof or other now known or later developed devices for displaying an image, a region of interest, region of interest information and/or user input information.

Modes of ultrasound used in medical imaging include the following:

A-mode: A-mode (amplitude mode) is the simplest type of ultrasound. A single transducer scans a line through the body with the echoes plotted on screen as a function of depth. Therapeutic ultrasound aimed at a specific tumor or calculus is also A-mode, to allow for pinpoint accurate focus of the destructive wave energy.

B-mode or 2D mode: In B-mode (brightness mode) ultrasound, a linear array of transducers simultaneously scans a plane through the body that can be viewed as a two-dimensional image on screen. Sometimes referred to as 2D mode, this mode is generally the starting point for exam types that use other modes.

C-mode: A C-mode image is formed in a plane normal to a B-mode image. A gate that selects data from a specific depth from an A-mode line is used; then the transducer is moved in the 2D plane to sample the entire region at this fixed depth. When the transducer traverses the area in a spiral, an area of 100 $cm^2$ can be scanned in around 10 seconds.

M-mode: In M-mode (motion mode) ultrasound, pulses are emitted in quick succession. With each pulse, either an A-mode or B-mode image is acquired. Over time, M-mode imaging is analogous to recording a video in ultrasound. As the organ boundaries that produce reflections move relative to the probe, this mode can be used to determine the velocity of specific organ structures.

Doppler mode: This mode makes use of the Doppler effect in measuring and visualizing blood flow.

Color Doppler: Velocity information is presented as a color-coded overlay on top of a B-mode image. This mode is sometimes referred to as Color Flow or color mode.

Continuous Doppler: Doppler information is sampled along a line through the body, and all velocities detected at each point in time are presented (on a time line).

Pulsed wave (PW) Doppler: Doppler information is sampled from only a small sample volume (defined in 2D image), and presented on a timeline.

Duplex: a common name for the simultaneous presentation of 2D and (usually) PW Doppler information. (Using modern ultrasound machines, color Doppler is almost always also used; hence the alternative name Triplex.).

Pulse inversion mode: In this mode, two successive pulses with opposite sign are emitted and then subtracted from each other. This implies that any linearly responding constituent will disappear while gases with non-linear compressibility stand out. Pulse inversion may also be used in a similar manner as in Harmonic mode.

Harmonic mode: In this mode a deep penetrating fundamental frequency is emitted into the body and a harmonic overtone is detected. With this method, noise and artifacts due to reverberation and aberration are greatly reduced. Some also believe that penetration depth can be gained with improved lateral resolution; however, this is not well documented.

Elastography mode: this mode maps the elastic properties of soft tissue. Tissue response indicating hardness or softness can yield diagnostic information about the presence or status of disease. For example, cancerous tumors are often noticeably harder than the surrounding tissue, and diseased tissue generally stiffer than healthy tissue.

Shear Wave Elasticity Imaging (SWEI) refers to a sonography method for mapping tissue elasticity, a tissue characteristic measured according to dimensional or movement response to the acoustic signal. Particularly useful for soft tissue measurement, the method employs the force of acoustic radiation from focused ultrasound to generate shear waves in the soft tissue. A tissue elasticity map can be formed by measuring shear wave propagation parameters using ultrasound or MRI (Magnetic Resonance Imaging).

The terms "Elasticity Imaging" and "Elastography" are typically viewed as synonymous, thus the acronym SWEI (Shear Wave Elastography Imaging) is often shortened to SWE (Shear Wave Elastography). The shear wave speed is governed by the shear modulus of tissue which is highly sensitive to physiological and pathological structural changes of tissue. Variation of the shear modulus may range over several orders of magnitude depending on the structure and state of tissue. This variation of the shear wave speed increases in many tissues in the presence of disease, e.g. known cancerous or tissues can be significantly stiffer than normal tissue. For this reason, the possibility of using shear waves in new diagnostic methods and devices has been extensively investigated over the last two decades.

Various parameters of tissue that characterize its structure and state such as anisotropy, viscosity, and nonlinearity, can be assessed using ultrasonic shear waves. Shear waves are polarized which makes them sensitive to tissue anisotropy, which is a structural anatomical characteristic that can have diagnostic value. By directing shear waves in different directions, some practitioners believe it is possible to more accurately characterize tissue anisotropy. Following this approach, the large frequency range of the shear wave that can be generated in tissue appears to have benefit for tissue diagnostics and to offer considerable potential for characterizing tissue viscoelastic properties. Shear wave attenuation is inherently high; thus, the directed acoustic shear waves do not propagate very deeply into the subject tissue. This is viewed by some as an advantage because the shear waves induced by acoustic radiation force are less prone to artifacts from reflections and interactions along other tissue boundaries.

In order to more precisely define the operation of the Applicants' method, it is useful to categorize ultrasound imaging modes according to the type(s) of acoustic signal used for each mode and whether or not the sensed measurement primarily obtains static position and dimensional information or measures movement, such as fluids movement, or response to acoustical signal variation. Using these general criteria, each ultrasound can be classified as one of either of the following:

(i) survey modes. This category includes more static ultrasound modes that primarily show position and dimension. Survey modes broadly enable the patient anatomy that is under study to be identified, located in space, and dimensioned, and includes A-mode, B-mode, C-mode, M-mode, and harmonic mode. The survey modes can be considered as mapping modes, using acoustic energy to identify and present the overall anatomy of interest as the overall ROI. Survey mode scanning is characterized by relatively low energy levels, moderate to low computational demands with relatively straightforward computation, and generates broader areas of image content, so that the image coverage is sufficient to include the region of interest and surrounding portions of the anatomy. In conventional practice, initial measurements of the patient are obtained in a survey mode and the ROI displayed accordingly. There are no anatomy-related constraints for imaging type for typical survey modes. B-mode imaging is the predominant survey mode used in standard practice, and is considered compatible with virtually all tissue types.

(ii) functional modes. This category includes more specialized, dynamic imaging modes that characterize changing aspects or features of the subject tissue, including tissue response over a range of frequencies and temporal attributes such as fluid or gas flow and flow velocity. Other attributes measured using functional mode imaging can include tissue stiffness or elasticity, for example. Functional modes provided with the typical ultrasound system can include shear wave imaging SWEI, as described in more detail herein, as well as various types of Doppler imaging, including color Doppler, continuous Doppler, pulsed wave Doppler, and pulse inversion. Functional modes may not be useful over the full ROI defined by the corresponding survey modes and can be limited in some applications where they are useful, according to anatomical characteristics. Some anatomical features are considered incompatible with particular functional modes, such as the liver capsule and SWEI imaging, for example.

It should be noted that the identified survey mode and functional mode categories can be used in any sequence that provides useful results; however, the general workflows for imaging typically begin with a survey mode to help orient the practitioner or sonographer to the anatomy being studied, and then follow with one or more functional modes. Moreover, survey modes can be repeated in a workflow, such as where it can be useful for the operator to obtain further definition of a particular location for subsequent functional mode imaging.

Reference is made to U.S. Pat. No. 9,597,041 (Claus et al.) entitled "Sequential image acquisition with updating method and system", incorporated herein by reference in its entirety.

While conducting an ultrasound exam in conventional practice, the sonographer may often switch manually between multiple ultrasound modes. For example, the sonographer first operates in a B-mode in order to coarsely locate the ROI. The sonographer then transitions to a Doppler mode before moving back to the B-mode. For some particular examinations, there are pre-set (or pre-determined or pre-defined) steps/modes that the sonographer must follow. That is, the ordered sequence of modes used in a particular exam type can be predefined for the operator.

For carotid artery imaging, for example, the exam typically follows a progression of modes such as: (i) B-mode for initial positioning and establishing reference coordinates of the sample volume; (ii) Color Flow mode for improved visualization of blood vessels; and (iii) Pulse wave Doppler mode for highlighting blood flow within the sample volume.

For heart imaging, the exam progression can use B-mode or M-mode imaging for auto-positioning of the cursor, followed by Color Flow or pulse wave Doppler modes.

The Applicant has noted that in combination modes (such as Color Flow and Doppler), the sonographer preferably optimizes the settings for each of the modes individually. Also, based on the physical orientation of the anatomy on the displayed image, some of the settings are optimized on a per patient basis. This per patient optimization does not lend itself to global customization.

When viewing an ultrasound image on the display, the particular area of the displayed image that is of interest to the sonographer or other practitioner is referred to as the Region of Interest (ROI) or ROI extent. As the sonographer conducts the examination and switches between modes, the size and position, as well as the apparent shape of the ROI may change. This can require that the operator readjust settings in order to more accurately show features of anatomy in the ROI.

The region of interest (ROI) can be defined in any of a number of ways. In conventional practice, the ROI is defined by multiple points or vertices that define a shape, such as defining a rectangle or other parallelogram by its four corners, for example. Alternately, the ROI can be defined by a point and a distance, such as an identified center point and a radius or function of the distance from the point to a single boundary. The distance may be, for example, any of a radius, circumference, diagonal, length or width, diameter or other characteristic of a shape. The region of interest can alternately be defined by a point and two distances, such as a distance to each of two boundaries. In another arrangement, the region of interest can be a pre-defined shape positioned around a point, such as a square, rectangle, oval or combination thereof.

For breast imaging using a breast imaging ultrasound system, the ROI may be a 3D region, as described in more detail subsequently.

The sonography workflow typically begins with acquisition of a grayscale mode image and display (such as the B-mode image illustrated in FIG. 4) in order to survey the anatomy. Depending on the exam type, the operator then switches to a different imaging mode such as Color Doppler mode (sometimes referred to as Color Flow mode or Color mode) to evaluate a sub-region of the originally viewed grayscale image in order to obtain additional clinical information and further characteristics of the anatomy or tissue within a particular ROI. The ROI in a polychromatic or color imaging mode can be indicated by a rectangular, parallelogram, trapezoidal or another regularly shaped outline. In a typical ultrasound system, the spatial extent of the color ROI is a partial subset of the larger B-mode image; some portions of the B-mode image may not be displayed in the subsequent color mode. This is because the computational processing demands for polychromatic presentation are significantly higher than those for grayscale B-mode processing and rendering; this is among the tradeoffs commonly established in conventional practice.

Figure 5:
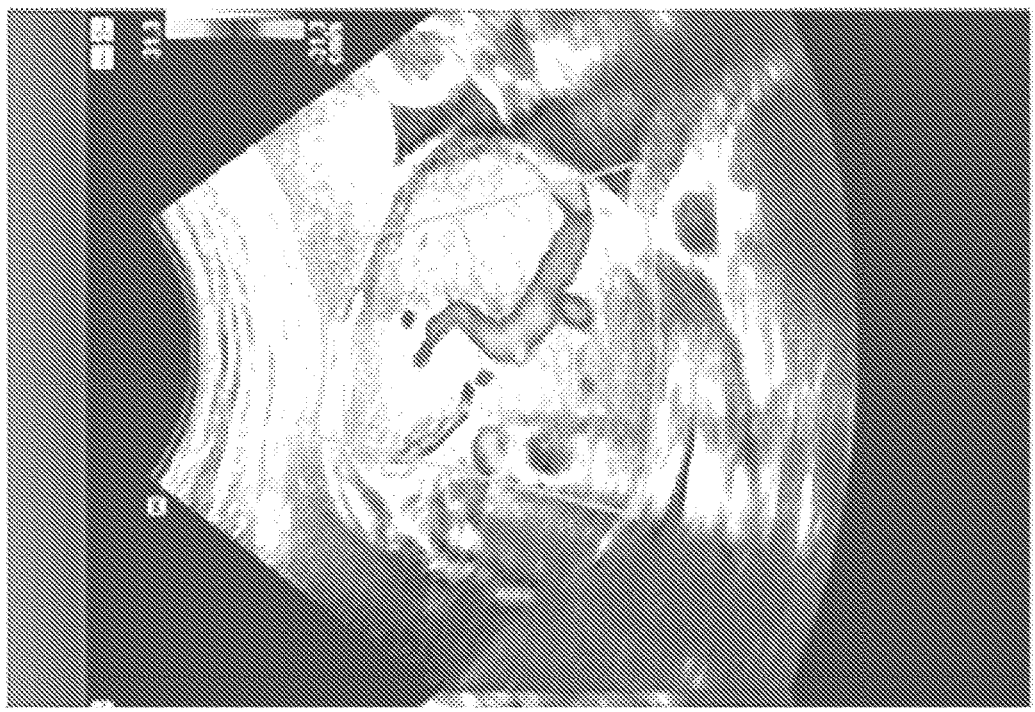
FIG. 5 shows a displayed ultrasound image having a region of interest, wherein a portion of the region of interest may be highlighted in brightness, contrast, color, or other image aspect.
Figure 4:
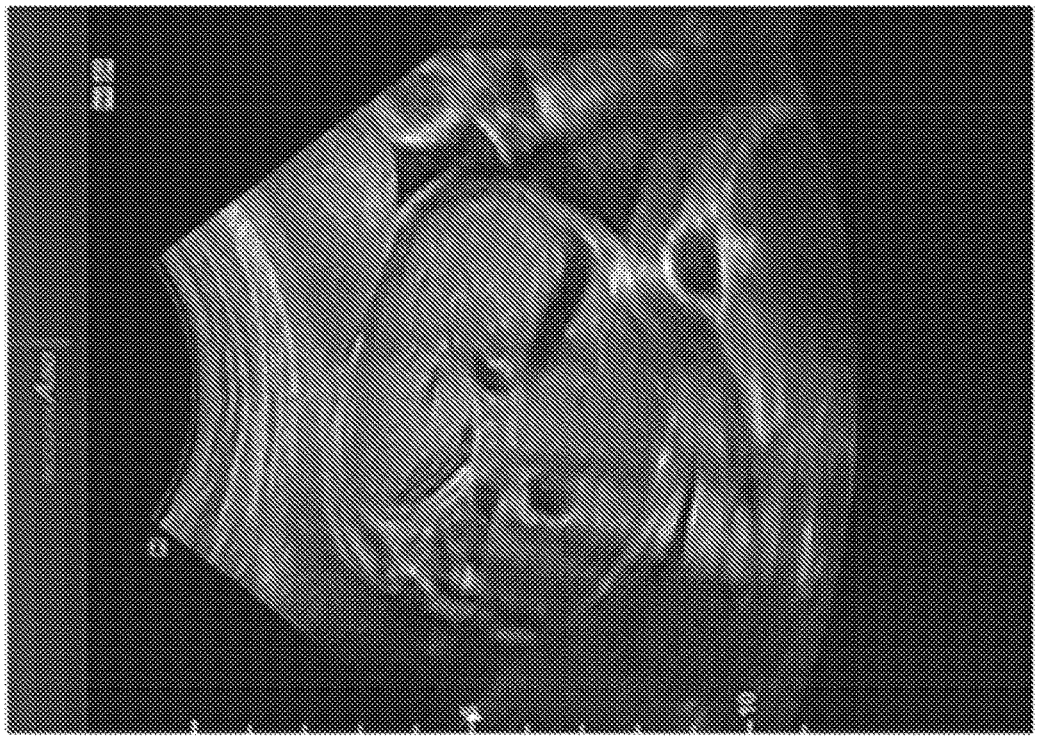
FIG. 4 shows a displayed ultrasound image having a region of interest, shown in grayscale.

By way of example, FIG. 4 shows B-mode ultrasound image, displayed as a grayscale image. FIG. 5 shows an image with the same ROI having color highlighting, obtained in Color Flow mode. Other types of highlighting can be used, including changes in brightness, contrast, annotation, or animation, for example.

A preferred embodiment can be described as a software program. Those skilled in the art will recognize that the equivalent of such software may also be constructed in hardware. Because image manipulation algorithms and systems are well known, the present description will be directed in particular to algorithms and systems forming part of, or cooperating more directly with, the method in accordance with the present invention. Other aspects of such algorithms and systems, and hardware and/or software for producing and otherwise processing the image signals involved therewith, not specifically shown or described herein may be selected from such systems, algorithms, components and elements known in the art.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The methods described above may be described with reference to a flowchart. Describing the methods by reference to a flowchart enables one skilled in the art to develop such programs, firmware, or hardware, including such instructions to carry out the methods on suitable computers, executing the instructions from computer-readable media. Similarly, the methods performed by the service computer programs, firmware, or hardware are also composed of computer-executable instructions.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "subject" is used to describe the patient that is undergoing ultrasound imaging. The terms "sonographer", "technician", "viewer", "operator", and "practitioner" are used to indicate the person who actively operates the sonography equipment.

The term "highlighting" for a displayed element or feature has its conventional meaning as is understood to those skilled in the information and image display arts. In general, highlighting uses some form of localized display enhancement to attract the attention of the viewer. Highlighting a portion of a display, such as a particular value, graph, message, or other element can be achieved in any of a number of ways, including, but not limited to, annotating, displaying a nearby or overlaying symbol, outlining or tracing, display in a different color or at a markedly different intensity or grayscale value than other image or information content, blinking or animation of a portion of a display, or display at larger scale, higher sharpness, or contrast.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

Portable Ultrasound systems are known, and the following references are incorporated herein by reference: U.S. Pat. No. 7,534,211 (Ultrasound cart with docking station); U.S. Pat. No. 9,180,898 (Ultrasound cart with flat surface); US 2008/0161688 (Tablet connected to cart); WO 2006/111874 A2; WO 2016/001865 A1 (Tablet connected to cart); WO2008068710A1 (Mobile Display); and CN102930170A (Video Glasses).

Figure 6:
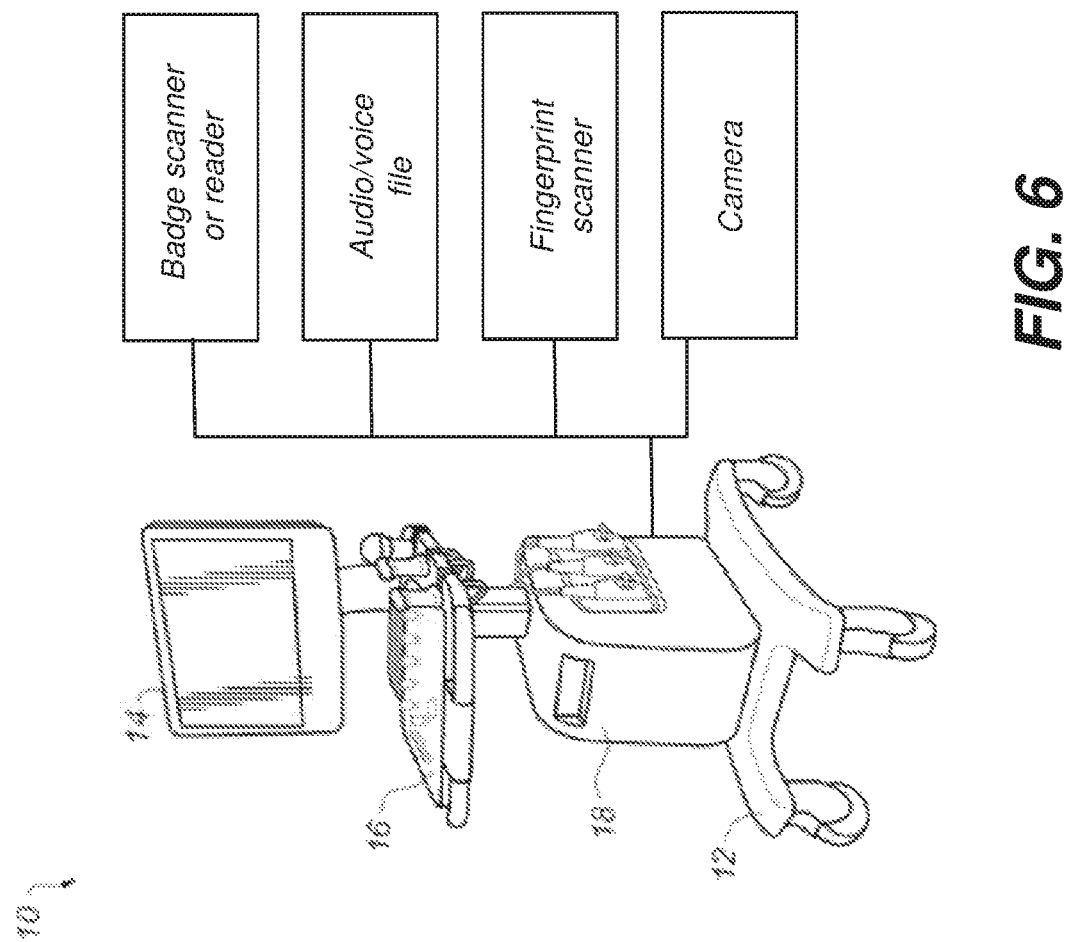
FIG. 6 shows an ultrasound system.

FIG. 6 shows an ultrasound system in accordance with the present disclosure. As illustrated, the ultrasound system can include one or more of the following: a camera; finger print reader/scanner; an audio or voice reader/scanner/detector; a badge/identification reader/scanner. Applicants have recognized the desirability for customizing the login and operating preferences of an ultrasound system. The customization of the login and/or preferences can be accomplished using any one of the elements: a camera; finger print reader/scanner; an audio or voice reader/scanner/detector; a badge/identification reader/scanner.

Embodiments of the present disclosure can be applied to any type of anatomy or automated exposure.

The acronym ABUS refers to an Automated Breast Ultrasound System. Automated Ultrasound refers to automatically performing an ultrasound scan of anatomy with little or no operator interaction during the scan. In known ABUS scanning devices, the operator places an ultrasound gel on the anatomy to be imaged. The operator then positions the scanning device in place over the anatomy and presses a button or enters other instruction to start the exam. The scanning device performs a sweep scan of the anatomy in one dimension, acquiring a series of 2D images from different positions along the scan path. From the series of 2D images, the system can produce a 3D image or even a 4D image (formed of 3D data viewed over time). The operator may perform multiple scans—including horizontal and vertical sweeps or axial, sagittal and coronal scans.

ABUS can be particularly useful for dense breasts, as traditional mammography may miss up to ⅓ of tumors in dense breast tissue. The exposure parameters used for dense and non-dense breast anatomy can vary widely. Since the ABUS scan is performed automatically without operator interaction, the system itself should determine the best parameters to use for the exposure and display of the image. This includes but is not limited to factors such as: Protocol & Preset Selection; Calculations; Operating Frequency; PRF; Gain; and Dynamic Range.

Figure 7A:
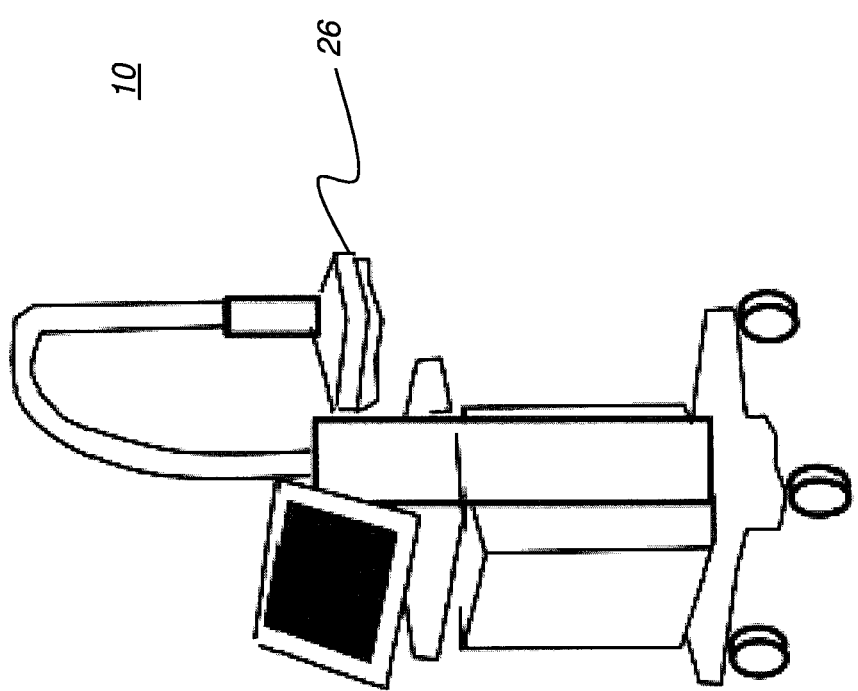
FIG. 7A shows an Automated Breast Ultrasound System that can provide automated scanning over selected tissue.
Figure 7B:
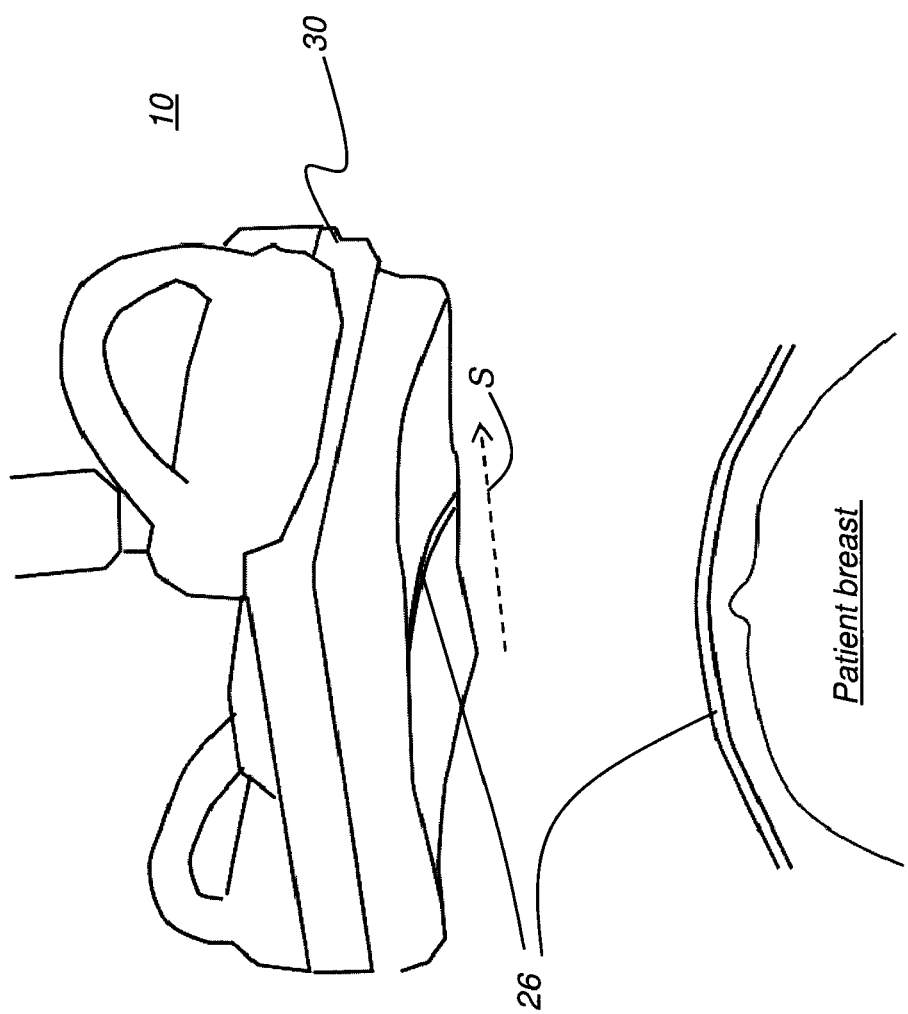
FIG. 7B shows a perspective view of a transducer apparatus for an ultrasound system.

The ABUS system has a special configuration, with a transducer probe arrangement that is particularly suitable for imaging of the breast. By way of example, FIG. 7A shows an Automated Breast Ultrasound System that can provide automated scanning over selected tissue. Probe 26 is mounted on the apparatus and configured for automated scanning of the breast. A transport apparatus 30 moves probe 26 in a scanning direction S. A close-up perspective view of probe 26 of ultrasound apparatus 10 is shown at the top of FIG. 7B, with a cross-sectional view of probe 26 curvature along the bottom portion of this figure.

Figure 8A:
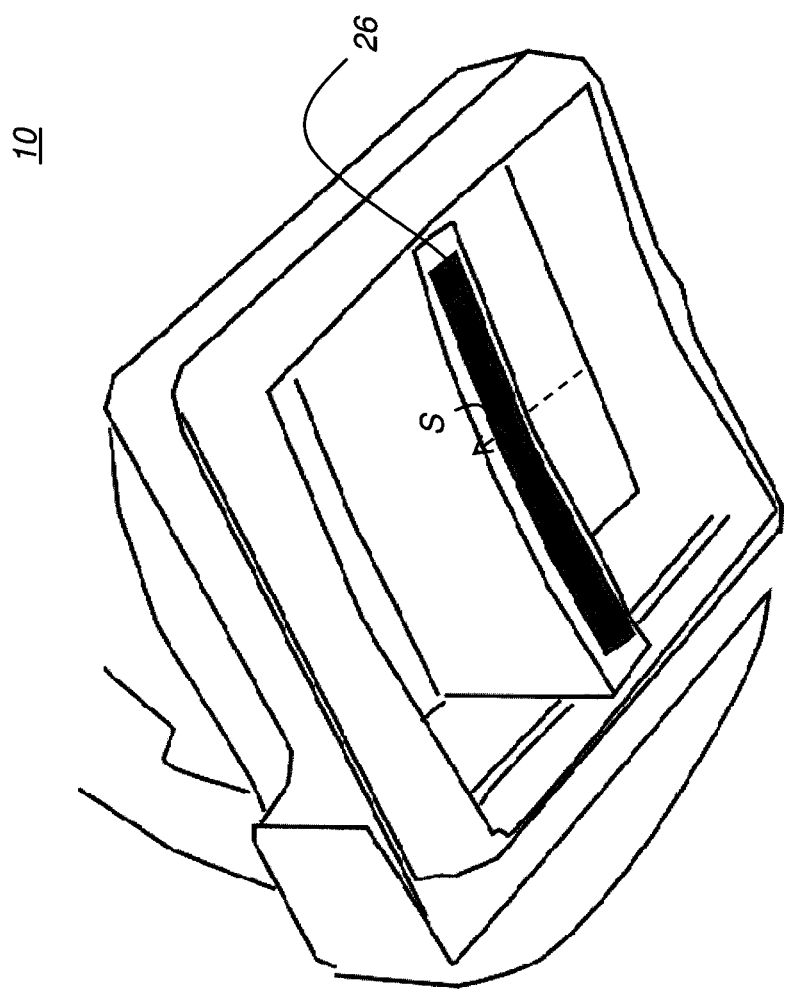
FIG. 8A shows a facing view of an automated transducer apparatus for an ultrasound system.

FIG. 8A shows a facing view of an automated transducer apparatus for an ABUS ultrasound system. Probe 26 is indexed across the subject anatomy in a scan direction S, orthogonal to the line of sensors of probe 26. It should be noted that probe 26 can be indexed in some other manner, such as rotated, for example.

Parameters Selection

Regarding parameters selection, determining parameters appropriate for the exposure can be done by means of:
(i) A pre-scan which can be performed at the same speed or at different (faster) speed than a normal scan. After acquiring this image data, the system can determine the best parameters to use for the scan.
(ii) Analysis of image content for the first or first several frames, using this information to determine parameters for the entire scan. After acquiring this image data, the system can determine the best parameters to use for the scan. The probe can acquire a number of frames while stationary at an initial position, before moving. These frames can then be analyzed to set parameters before further probe movement.
(iii) Exposure parameter adjustment on-the-fly from image analysis as the scan is being performed, which may be advantageous as breast size, density, and other features can change over areas of the breast anatomy. Variables such as signal type and scan speed can be dynamically adjusted based on sensed results.
(iv) Instead of using image content analysis to determine ideal, fixed parameters used throughout the scan, the system could vary the parameters and monitor image quality to determine which parameters yield the best image. The scan can even pause in response to poor signal or image quality or if conditions suggest the usefulness of other types of ultrasound data.
(v) A pre scan image could be displayed to the operator who can then adjust exposure parameters until satisfactory results are obtained.
(vi) Operator preselection of a breast density value which is used to determine which set of parameters to use.
(vii) Operator preselection of an anatomical region, body part, protocol, or preset which is used to determine which set of parameters to use.

Regarding variable image quality, the system preferably supports multiple scan speeds to allow for image quality/scan time tradeoffs. For example, operator selections may set up imaging at slower speeds, acquiring more image data at higher resolution, allowing imaging with smaller 2D image pixels or 3D image voxels. In an embodiment, parameter selection is an aspect of protocol selection. Scan speed can be determined by the operator preselection of anatomical region.

Flexible Transducer

Regarding the flexible transducer, a flexible transducer can apply multiple pressure levels against the anatomy. It is preferred to maintain contact with the anatomy across the entire width of the transducer, while not applying excessive pressure that might adversely affect image quality. For an ABUS system, the transducer element has curvature to conform to the shape of the breast, as suggested in FIG. 7B. However, breast size can vary from one patient to the next. A flexible transducer allows application of consistent pressure at each element across the entire width of the transducer, while adjusting the curve of transducer to conform to the anatomy. The transducer preferably comprises multiple crystals, allowing the emissive elements to shift slightly in position relative to each other.

Figure 8B:
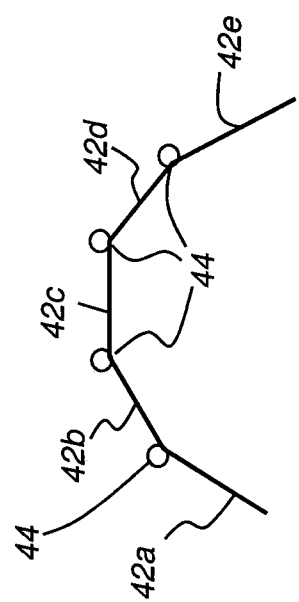
FIG. 8B shows a hinged transducer arrangement for an ultrasound apparatus.

The transducer is preferably made of a flexible material. Alternately, as shown in FIG. 8B, a stiff or rigid material that is in hinged sections 42a, 42b, 42c, 42d, 42e or otherwise allows flexure between sections can be used to form a transducer probe 40. Hinges 44 can be spring hinges or tension hinges, for example. The transducer can curve or adjust angularly at each section, or may be variably rigid, with a hinge mechanism adjustable over a series of one or more sections. The transducer curve may be determined due to pressure being applied on the transducer toward the anatomy. The conformal shape of the transducer can thus be changed over the course of a breast scan, for example. According to an embodiment, the transducer probe changes shape according to the contour of the imaged anatomy.

Location/Position Tracking

Regarding Location/Position Tracking, the relative angle of each ultrasound signal emission and sensing element is known so as to properly display the image and to construct a 3D image. Sensors or encoders can be used at each hinge point in order to sense the amount of flex in the transducer. When performing multiple scans on the same anatomy, sensors indicate the location of the transducer during each sweep so that the scan data can be correlated for each scan, providing higher image quality and correlating regions of interest in each scan. These sensors can be encoders in the arm holding the transducer, inclinometers that report angle information, or other sensors disposed to determine the relative position of the transducer between subsequent scans.

According to an embodiment, the operator selects a region of interest (ROI) in one scan and is shown that same image area region of interest on another scan. Another method of knowing the relative location of the transducer between scans is to automatically index the transducer between each scan. The base holding and transporting the transducer allows it to rotate 90 degrees between scans. Alternatively, the transducer can perform the exam by revolving about the anatomy in a circle.

Automating Scanning Sequence for Additional Scans

Regarding Additional Scans, typically automated ultrasound scans are B-Mode only scans. This behavior could be enhanced to include other modes, including: A-Mode or including Therapeutic Ultrasound; C-Mode; M-Mode; Doppler (Color, CWD, PW); Doppler Ultrasonography; Pulse Inversion; Motion Mode; Harmonic Mode; Elastography/ARFI (acoustic radiation force impulse); Compression Ultrasonography; Contrast Ultrasonography; Molecular Ultrasonography; SWEI; or Phased Contrast Imaging. Any combination of these modes can be conducted as part of the same exam.

Figure 9:
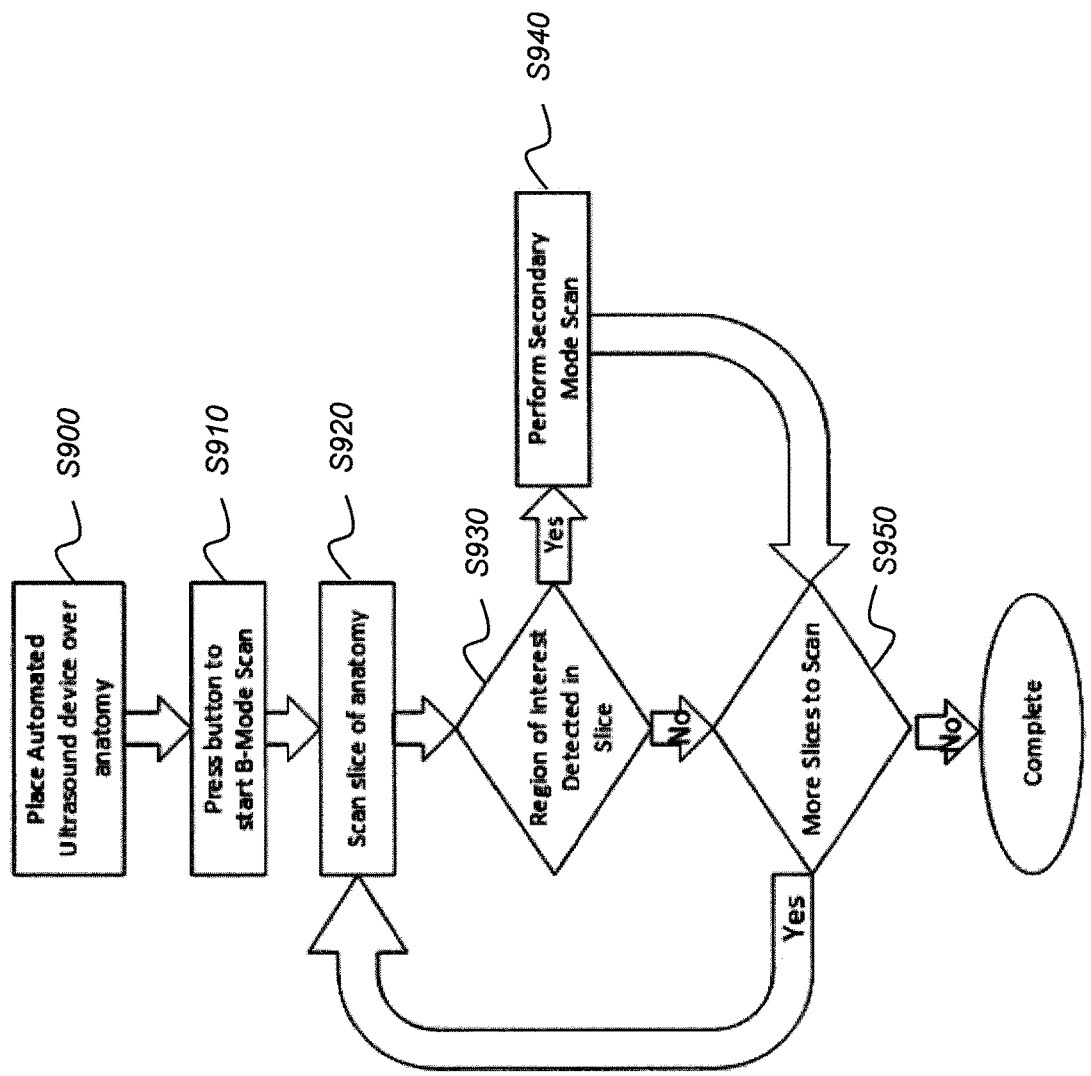
FIG. 9 shows a flowchart in accordance with the present disclosure regarding a secondary mode.
Figure 10:
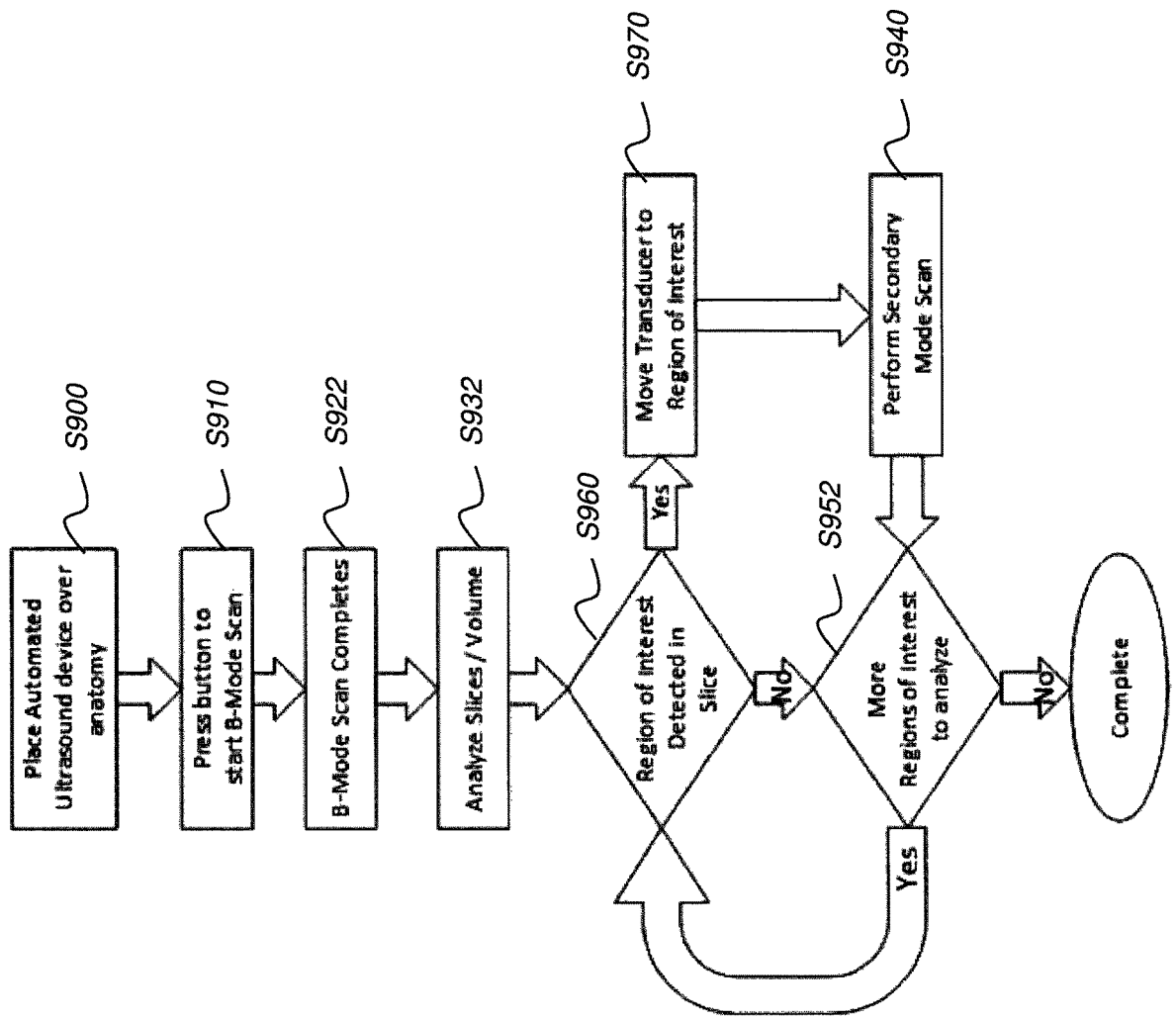
FIG. 10 shows a flowchart in accordance with the present disclosure similarly showing a sequence having a secondary mode.

Reference is now made to the logic flow shown in FIGS. 9 and 10. Regarding Automatic Additional Scans, an Automated Ultrasound system can automatically perform a secondary scan when it automatically detects a region of interest. This additional secondary mode scan could be performed during the B-Mode survey sweep, such as using the process shown in FIG. 9, or could be performed subsequent to the full B-Mode initial scan as shown in the FIG. 10 sequence, during a separate transducer re-positioning and secondary scan.

In the FIG. 9 sequence, the operator prepares the patient in a preparation step S900, such as providing support for the examined anatomy and applying any needed gel material onto the skin surface. In a scan initiation step S910, a B-mode or other scan is initiated. An acquisition step S920 acquires a scanned image. An analysis step S930 then determines whether or not the acquired image has any features of interest. By way of an example, results from a B-Mode scan in step S920 may be analyzed in step S930 to detect a lesion or other feature that could be cancer, such as by using CAD (Computer Aided Detection). Where the ROI contains a feature that suggests the need for additional scanning, a secondary mode scanning step S940 executes. In the example given, the system can automatically perform an Elastography/ARFI scan on the identified tissue to determine the mechanical properties of the tissue to aid in cancer diagnosis. Processing then moves to a check step S950 that determines whether or not there are additional slices to scan. If so, processing returns to acquisition step S920 for the next scan. If not, the automated scan process terminates. The mode for secondary mode scanning step S940 can alternately be determined by an operator selection of the anatomy or anatomical region to be scanned.

FIG. 10 shows an alternative sequence in which the CAD analysis is performed upon completion of the B-mode scanning sequence for multiple image slices in a volume. An acquisition step S922 continues until all portions of the target anatomy are scanned in B-mode. An analysis step S932 then analyzes multiple slices or a reconstructed volume from the completed B-mode scans. A detection step S960 determines whether or not a particular slice contains the detected feature of interest and executes a transducer positioning step S970 accordingly when the ROI is detected. Step S970 uses coordinate information obtained from the B-mode scanning sequence in order to determine transducer position and orientation for acquiring additional scan data. A check step S952 determines whether or not there are additional slices to analyze and terminates or continues processing according to detected results.

In another example that follows either FIG. 9 or FIG. 10 accordingly, a B-Mode scan detects a blood vessel and records heart rate information using Pulse-Width Doppler (PWD).

The secondary modes used in step S940 could be any of the following: A-Mode; M-Mode; Doppler (Color, CWD, PW); Doppler Ultrasonography; Pulse Inversion; Motion Mode; Harmonic Mode; Elastography/ARFI (acoustic radiation force impulse); Compression Ultrasonography; Contrast Ultrasonography; Molecular Ultrasonography; SWEI; or Phased Contrast Imaging.

The following observations can be made:
 a) Each 2D image of the primary scan is analyzed before moving the transducer as in FIG. 9. If a region of interest (ROI) is identified, then the system performs the configured secondary scan.
 b) The entire scan is completed, then the image data is analyzed, as in FIG. 10, possibly after reconstructing a 3D image. The transducer then returns to any identified region of interest to perform a secondary scan of that area in step S940.

c) The entire scan is completed then the operator is shown the acquired image. The operator highlights a region of interest as a point or as a 2D or 3D area. The transducer then returns to any identified region of interest to perform a secondary scan of that area as specified by the operator.

d) Multiple scan modes could be performed together automatically by default, without detection of a region of interest. Then the operator can view one or multiple modes individually or simultaneously, such as overlaid on top of each other.

e) Secondary scans could also be performed in 2D, requiring the transducer to move during the second mode scan.

It is noted that the operator can have the ability to indicate if secondary scanning is performed and to designate what type of secondary mode scan executes based on what region of interest is identified in the primary scan.

ROI Detection

Regarding Detection of Region of Interest (ROI), the analysis can be based on any of the following using the FIG. 9 or 10 sequence:

a) Current slice of data, including data acquired from the most recent transducer location;

b) Current slice plus all previously acquired slice data accumulated up to this point, for partial scan data;

c) All slice data collected after the scan is complete;

d) 3D reconstruction based on slices that have currently been acquired; or e) 3D reconstruction based on slice data after the scan is complete.

It is noted that 3D reconstruction may be dependent on Electronic 3D Steering

ROI detection can be based on factors such as pronounced difference from one intensity value to the next, either in line with the transducer probe sensor detection or along the direction of the scan from one sensed line to the next. This could indicate areas of relatively high density where not expected, for example. According to an embodiment of the present disclosure, B-mode imaging is used for initial detection, followed by shear mode or elastography detection as a secondary mode where an ROI is detected. The shear mode detection can be focused at the ROI area only or can be directed to the entire line of transducer probe sensors.

An embodiment of the present disclosure can automatically determine and perform a secondary scan interspersed with the primary scan. The primary scan is a survey mode, as defined previously, such as B-mode imaging. The secondary scan is performed selectively and is generally a functional mode, such as shear wave (SWEI) imaging for elastography or other tissue quality detection.

Artificial intelligence (AI) techniques such as neural network or other types of pattern recognition can be employed for ROI detection. Advantageously, ultrasound exposure is harmless to patient tissue. Thus, even a slight irregularity in tissue density or other quality can be sufficient to cause the ultrasound system to switch to secondary mode imaging at any point along the scan. As the scan indexes from one position to the next, a slice of the tissue is imaged. The collection of slices thus obtained can be used to form a 3D image of the breast or other imaged anatomy.

Embodiments of the present disclosure can automatically adjust scan parameters for both the primary and secondary modes according to analysis of the imaged tissue. For breast imaging, for example, adjustments can be dynamically made depending on detected tissue quality, such as for homogeneously dense, heterogeneously dense, scattered fibroglandular tissue, or where implants are detected, as well as for overall tissue thickness in the imaged area.

The system display can highlight the position of one or more detected regions of interest, such as using color, animation, or other visible display effect. The system can also provide a link or control button that actuates the system to display image content for a region of interest.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A computer implemented method for ultrasound imaging, the method comprising:

obtaining a plurality of ultrasound images during an ultrasound exam of a patient body part using a transducer probe at a first position in a primary imaging mode, the transducer probe comprising a directionally oriented array of ultrasonic elements;

analyzing the obtained ultrasound images of the patient body part, including detecting a region of interest in the obtained ultrasound images of the patient body part;

responding to the detected region of interest by automatically switching the transducer probe to a secondary imaging mode, with the transducer probe at the first position; and automatically indexing the directionally oriented array of ultrasonic elements to a different angular position relative to the transducer probe, with the transducer probe at the first position, and obtaining ultrasound images of the patient body part in the second imaging mode and with the directionally oriented array of ultrasonic elements at the different angular position.

2. The method of claim 1, wherein the secondary imaging mode is a shear wave elasticity imaging mode that obtains elastography image data.

3. The method of claim 1, wherein the patient body part is a human breast.

4. The method of claim 1, wherein the step of automatically indexing is performed automatically by a transport apparatus.

5. The method of claim 1, further comprising selecting the secondary mode from the group consisting of color Doppler, continuous Doppler, pulsed wave Doppler, and pulse inversion modes.

6. The method of claim 1, further comprising automatically determining the secondary imaging mode in response to an operator selecting the patient body part.

7. The method of claim 1, further comprising automatically determining a scan speed of the transducer probe for one or both of the primary and secondary imaging modes in response to an operator selecting the patient body part.

8. The method of claim 1, wherein the step of analyzing includes automatically determining a scan speed for one or both of the primary and secondary imaging modes.

9. The method of claim 1, further comprising positioning the ultrasonic elements in a first line during the primary imaging mode, wherein the different angular position of the array of ultrasonic elements is along a second line orthogonal to the first line of the ultrasonic elements.

10. The method of claim 1 further comprising highlighting the detected region of interest on a display.

11. The method of claim 1 further comprising providing a link to display image content for the detected region of interest.

12. A method for ultrasound imaging of a breast of a patient, the method comprising:
providing a linear array of ultrasonic transducer elements secured in position in a transducer probe;
emitting and detecting ultrasound signals using the linear array of ultrasonic transducer elements in a first imaging mode;
analyzing the detected ultrasound signals to determine a region of interest within the breast of the patient;
responding to the determined region of interest by automatically switching the linear array of ultrasonic transducer elements to a second imaging mode and rotating the linear array of ultrasonic transducer elements relative to the transducer probe; and
emitting and detecting ultrasound signals using the linear array of ultrasonic transducer elements in the second imaging mode and at the rotated position.

13. The method of claim 12, further comprising highlighting the determined region of interest on a display.

14. A computer implemented method for ultrasound imaging of a breast, the method comprising:
providing a transducer probe having a linear array of ultrasonic transducer elements;
emitting ultrasonic signals and obtaining ultrasound images of the breast using the transducer probe in a first imaging mode;
analyzing the ultrasound images to detect a region of interest within the ultrasound images of the breast;
in response to detecting the region of interest, automatically indexing the transducer probe by rotating the linear array of ultrasonic transducer elements, relative to the transducer probe, to a sequence of successive imaging positions; and displaying the region of interest within the ultrasound images of the breast an image generated by the steps of detecting and indexing.

15. The method of claim 14 further comprising:
automatically switching the transducer probe to a secondary imaging mode before the step of automatically indexing the transducer probe.

16. The method of claim 14, further comprising rotating the linear array of ultrasonic transducer elements 90°.

* * * * *

UNITED STATES PATENT AND TRADEMARK OFFICE
CERTIFICATE OF CORRECTION

PATENT NO. : 10,912,536 B2  
APPLICATION NO. : 15/681887  
DATED : February 9, 2021  
INVENTOR(S) : Michael C Lalena Page 1 of 1

It is certified that error appears in the above-identified patent and that said Letters Patent is hereby corrected as shown below:

In the Claims

Column 16, Claim 14, Line 23-24  Please remove "an image generated by the steps of detecting and indexing"

Signed and Sealed this  
Twenty-fourth Day of August, 2021

Drew Hirshfeld  
*Performing the Functions and Duties of the*  
*Under Secretary of Commerce for Intellectual Property and*  
*Director of the United States Patent and Trademark Office*